May 18, 1943. J. J. GRULLEMANS Plant Pat. 584

ASTER

Filed Nov. 5, 1942

WITNESS

Addison E. Avery

INVENTOR

JOHN J. GRULLEMANS

BY John H. Leonard his ATTORNEY

Patented May 18, 1943

Plant Pat. 584

UNITED STATES PATENT OFFICE

584

ASTER

John J. Grullemans, Painesville, Ohio, assignor to The Wayside Gardens Company, Mentor, Ohio, a corporation of Ohio Application November 5, 1942, Serial No. 464,583

1 Claim. (Cl. 47—60)

This application for Letters Patent is for a novel and distinct variety of aster or Michaelmas Daisy, being more particularly a selected form of *Aster novae-angliae*, said form having been selected from several hundred plants resulting from hand pollinated seed plants grown in a nursery, which seed plants were of a variety of *Aster novae-angliae* formerly known as "Survivor." The plant so formerly known was both seed and pollen parent of the present plant. The parent stock has been destroyed since the discovery, development and asexual reproduction of the present plant took place.

Figure 1:
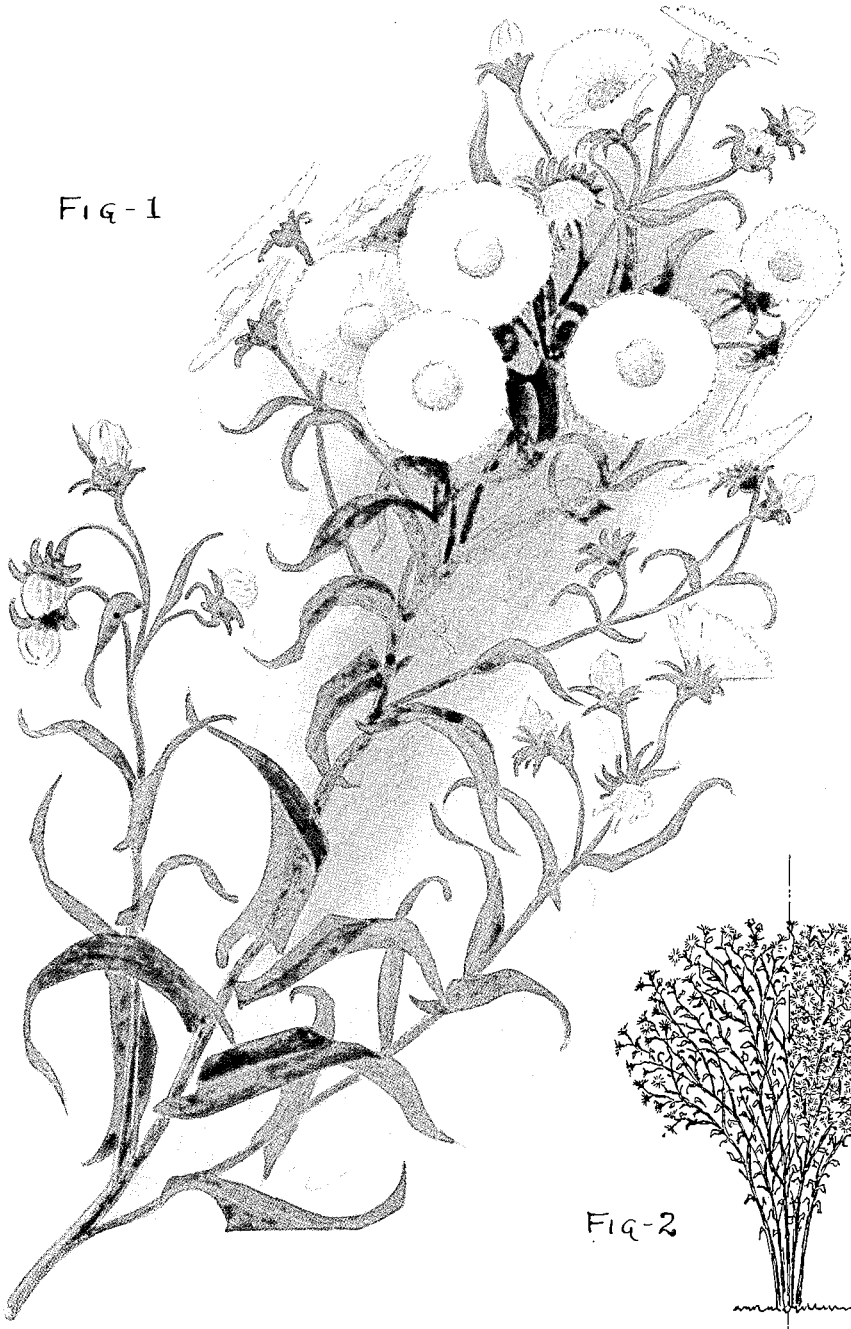
Figure 2:
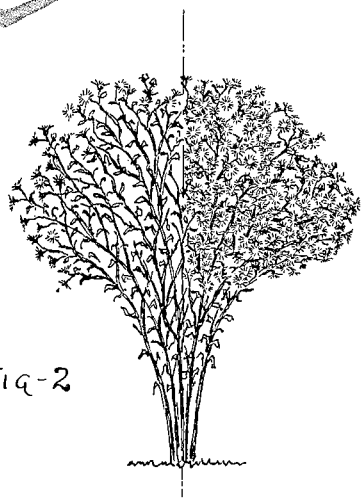

The drawing, Fig. 1 illustrates the flower and part of the plant and Fig. 2 shows certain characteristics of the growing habit of the plant.

The aster is a hardy perennial. I first discovered and observed the plant in the fall of 1941 in the nursery of The Wayside Gardens Company, Mentor, Ohio, growing in a row of selected hand pollinated seedlings. I have reproduced the present plant asexually, through plant division.

The plant is an upright, vigorous growing aster, and normally attains a height of from three and one-half to four and one-half feet, being distinguished from the parent stock in the matter of height, said parent stock growing normally from six to eight inches taller under substantially the same conditions of soil and weather and with more tendency to sprawl. The present plant is ordinarily bare of leaves or branches up to a height of from six to ten inches from the ground, but thereabove it is well and stiffly branched so that it has a formal bush-like appearance. Generally, the present plant is a great improvement over the large purple aster, Michaelmas Daisy, which is well distributed throughout the north central portion of the United States, being a more upright grower, neater in appearance, more compact and shorter.

The plant has abundant light green leaves which are acute, rather thick and pubescent and arranged in clasping relation to the stem. The plant is perfectly hardy in Ohio and has the typically high resistance to diseases and pests of all varieties of this species.

As compared to the parent stock and most Novae-angliae asters, the branches at the outside of the present plant, which tend to sprawl in the usual manner, bear flower stalks which, contrary to most Novae-angliae asters, turn upwardly rather abruptly and assume a generally upright position at their terminals, in a manner to lift all the flowers well off the ground and form a much more compact upper structural plant growth which is well covered with flowers although the flowers do not crowd each other. The drawing Fig. 2, shows more or less diagrammatically, and particularly at the left half of the view which exhibits the plant as though in central cross section, the manner in which the outlying stalks have such more upwardly turned flower bearing branch portions than Novae-angliae asters usually have.

Generally, in Ohio, the flowering season of the present aster is at its best from the last week in September to and including the first half of October, as compared to the well-known Harrington's Pink, which, in the same locality, under the same conditions, is in full flower by September 20th, and of which the flowering period terminates about the first of October. For a more direct comparison, the present aster blooms somewhat later than the parent stock, and fully two weeks later than Harrington's Pink. It is the latest blooming pink aster known to me at the present time.

The petals are Pink, comparable, when unshadowed, to Maerz and Paul chart, Plate 1–K–8, in some instances ranging to 1–F–7. The coloring of the flower is very uniform except for a slight, but not objectionable, bleaching with age. The petal color as viewed in the field on a fairly bright day is a true Pink without any noticeable trace of Lavender, and if anything, very slightly toward Salmon Pink. The petals upon close observation, are substantially identical in color with Harrington's Pink, but when viewed as a mass in the field, particularly toward or away from the sun, the color of the flowers is a more intense and purer Pink than that of the flowers of the parent stock from which the present plant was derived.

The central disc is Yellow comparable to Maerz and Paul Plate 10–L–4. The petals are of relatively thin texture, linear and elongated in form, the apex of each petal being acute. The petals extend radially from, and are regularly spaced apart from each other about the disc, giving the flower an open, delicate and beautiful open ray appearance. The petals have a slight camphor-like aroma, are of excellent lasting qualities on the plant and of fair lasting qualities on the cut flower. The stamens are composite with Yellow pollen comparable to Maerz and Paul Plate No. 10–L–4, the styles and ovaries being unexposed.

The flowers are borne in panicles, are daisy-like in form having a distinctly open ray appearance and average about one and one quarter inches in diameter. They have a central disc about three-eighths inch in diameter.

The permanence of the bloom is good, the spent blooms not being unsightly as with many varieties of aster. The upper half of the plant is covered completely with blooms, so that at a distance it appears to be a large mass or bouquet of pink blooms. The blooms retain their pure pink color throughout the blooming period.

The aster is distinguished from asters generally in the beauty and purity of its Pink color in which it surpasses Harrington's Pink. It is further distinguished from other Pink novae-angliae asters, including Harrington's Pink, in that the petals are linear and are narrower, longer, and less curved, thus imparting flatness and greater diameter to the flower. It is further distinguished by the good lasting qualities of the flowers and of the color of the petals and the beauty of the flowers throughout the blooming season. In addition to the distinguishing characteristics of the flower, the plant as a whole is distinguished from other Novae-angliae asters in that it is of more vigorous growth; has a later blooming period; has the more open form of branching, and has a more upright growth or manner of bearing its flowers so as to be bush-like and generally upright in general appearance.

Having now fully shown and described my new aster, and the mode of its production, what I claim and desire to secure by Letters Patent of the United States is:

A new hybrid Novae-angliae aster as herein shown and described; the plant being characterized by its vigorous and generally upright but bush-like, dense and compact growth, tendency of outlying, bloom bearing branches to turn upwardly at their ends and to maintain the blooms borne thereby well off the ground, and by an unusually late blooming habit; and the flowers being characterized particularly by their intense and pure pink color and generally flat disc-like open ray form with comparatively straight, relatively narrow and uniformly spaced petals.

JOHN J. GRULLEMANS.